(12) United States Patent
Sutoh

(10) Patent No.: US 8,246,535 B2
(45) Date of Patent: Aug. 21, 2012

(54) BENDING INSTRUMENT FOR AN ENDOSCOPE AND ENDOSCOPE SET

(75) Inventor: Dai Sutoh, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 940 days.

(21) Appl. No.: 12/277,107

(22) Filed: Nov. 24, 2008

(65) Prior Publication Data

US 2009/0171154 A1    Jul. 2, 2009

(30) Foreign Application Priority Data

Dec. 27, 2007  (JP) ................................ 2007-336151

(51) Int. Cl.
*A61B 1/00* (2006.01)
(52) U.S. Cl. ......... 600/114; 600/107; 600/115; 600/146
(58) Field of Classification Search .................. 600/107, 600/114–115, 146
See application file for complete search history.

(56) References Cited

U.S. PATENT DOCUMENTS

| | | | |
|---|---|---|---|
| 4,688,554 A * | 8/1987 | Habib ........................... | 600/114 |
| 4,773,394 A * | 9/1988 | Reichstein et al. ........... | 600/114 |
| 5,306,245 A | 4/1994 | Heaven | |
| 5,935,107 A * | 8/1999 | Taylor et al. ............. | 604/164.04 |
| 6,099,464 A | 8/2000 | Shimizu | |
| 6,174,280 B1 | 1/2001 | Oneda et al. | |
| 7,182,864 B2 * | 2/2007 | Brown et al. ................. | 210/232 |
| 7,931,661 B2 * | 4/2011 | Saadat et al. .................. | 606/144 |
| 8,066,673 B2 * | 11/2011 | Hart et al. ................ | 604/164.03 |
| 2007/0016134 A1 * | 1/2007 | Suzuki et al. ................. | 604/104 |
| 2008/0119868 A1 * | 5/2008 | Sharp et al. ................... | 606/119 |

FOREIGN PATENT DOCUMENTS

| | | |
|---|---|---|
| JP | 08280694 | 10/1996 |
| WO | 98/26724 A | 6/1998 |

OTHER PUBLICATIONS

European Search Report for EP 08 170 917.2 dated Mar. 11, 2009, 4 pgs.
Office Action issued Nov. 9, 2011 from related Taiwan Patent Application U.S. Appl. No. 097148814, 3 pgs—English Translation.

* cited by examiner

*Primary Examiner* — Matthew J Kasztejna
(74) *Attorney, Agent, or Firm* — Elias Domingo

(57) ABSTRACT

A bending instrument for an endoscope which is used when a fiberscope is inserted into a gastrostomy catheter. The bending instrument comprises a sheath which covers a fiberscope shaft of the fiberscope, and a bending member which allows the fiberscope shaft to bend together with the sheath. A light-transmissive window part is formed at the tip end of the sheath. Furthermore, the bending member comprises a fixed part which is attached to the tip end outer periphery of the sheath, a sliding part which is slidably attached further to the base end side of the sheath than the fixed part and which engages with a cylindrical engagement part of the gastrostomy catheter so as not to be able to go past an intra-stomach fixed part, and a linear linking part which links the fixed part and the sliding part.

4 Claims, 13 Drawing Sheets

BENDING INSTRUMENT FOR AN ENDOSCOPE AND ENDOSCOPE SET

FIELD OF THE INVENTION

The present invention relates to a bending instrument for an endoscope which is used when a gastrostomy catheter is indwelling in a gastrostomy hole formed in a patient's body, and an endoscope is inserted into said gastrostomy catheter to observe the interior of the stomach, and to an endoscope set provided therewith.

BACKGROUND OF THE INVENTION

The stomach wall or the like of a patient is conventionally observed by inserting an endoscope nasally or orally into the stomach, or the like, but this method can cause discomfort to the patient. Consequently, it has become necessary in recent practice to make a gastrostomy catheter indwelling in a gastrostomy hole formed in the patient's body and to observe the interior of the stomach by passing an endoscope inside said gastrostomy catheter so as to confirm the indwelling position of the gastrostomy catheter. In such cases it is necessary to be able to change the orientation of the tip end of the endoscope for observation in various directions in order to accurately check the state of the interior the stomach and to confirm the indwelling position of the gastrostomy catheter. Consequently, a bending instrument for an endoscope in which the direction of orientation of the tip end of the endoscope can be changed is used (see Japanese Unexamined Patent Application Publication H8-280694, for example).

This bending sheath for a probe (bending instrument for an endoscope) has a configuration in which one end of a metal wire is fixed by soldering to a metal fixture of the bending sheath which is provided with the metal fixture at one end and provided with a metal fixture for the forceps hole at the other end, and a metal cap is fixed by soldering to the other end of the wire. A probe (endoscope) to which this bending sheath for a probe is fitted comprises an ultrasonic probe which is provided with an ultrasonic oscillator at the tip end, and said ultrasonic probe is connected to a device which can produce images from ultrasonic tomographic images on an ultrasonic monitor by sending and receiving ultrasonic waves to the patient via the ultrasonic oscillator.

Consequently, the ultrasonic probe is inserted into the bending sheath from the metal fixture for the forceps hole and the tip end thereof runs into the inner wall of the cap, after which, with continued insertion of the ultrasonic probe, the portion at the tip end of the ultrasonic probe starts to bend so as to move away from the axial direction of the bending sheath. By means of this, the tip end of the ultrasonic probe can be oriented in the required direction, making it possible to obtain ultrasonic tomographic images of that area.

However, with the bending sheath for a probe described above, the bending sheath and the cap are joined to the wire, and therefore a portion of the ultrasonic probe lying between the bending sheath and the cap is exposed to the outside. Consequently, the exposed portion of the ultrasonic probe comes into direct contact with bodily fluids etc. from various parts of the body during use, and becomes soiled. Furthermore, with the bending sheath for a probe described above, the cap comprises a member that is closed at its tip end, and therefore it cannot be used with an endoscope for capturing images by focusing using a lens.

The present invention has been devised in order to deal with the problems described above, and it aims to provide a bending instrument for an endoscope with which it is possible to observe various parts inside the stomach using an endoscope, without soiling of the endoscope, and an endoscope set which employs this.

SUMMARY OF THE INVENTION

In one aspect, the invention is directed to a bending instrument for an endoscope a tubular part formed with an internal through-hole, and an intra-stomach fixed part which is joined to the tip end of the tubular part in a state in which the tip end of the through-hole of the tubular part is open and which is provided with an engagement part in the vicinity of the tip end of the through-hole. The bending instrument is used when an endoscope is inserted into an indwelling gastrostomy catheter such that the tubular part is positioned in a gastrostomy hole formed between the surface of a patient's skin and the inner surface of the stomach wall and also such that the intra-stomach fixed part is positioned inside the stomach. The bending instrument for an endoscope comprises: a sheath; a bending member; a sliding part; and a linking part. The sheath can pass inside the gastrostomy catheter together with the endoscope in a manner such that it covers the endoscope, and it has a light-transmissive window part formed at its tip end. The bending member comprises a fixed part which is attached to the tip end outer periphery of the sheath in a manner such that it cannot move to the base end side of the sheath and such that it can pass inside the gastrostomy catheter together with the sheath. The sliding part is slidably attached further to the base end side of the sheath than the site of attachment of the fixed part, and can pass through the through-hole of the gastrostomy catheter, but engages with the engagement part of the intra-stomach fixed part so as not to be able to go past the intra-stomach fixed part. The linking part links the fixed part and the sliding part, thereby controlling the gap between the fixed part and the sliding part so that it does not exceed a specified length.

DESCRIPTION OF FIGURE NOTATIONS

10 . . . gastrostomy catheter;
12 . . . tubular part;
13 . . . intra-stomach fixed part;
18*a* . . . cylindrical engagement part;
20 . . . fiberscope;
21 . . . fiberscope shaft;
30 . . . bending instrument for endoscope;
31, 51 . . . sheath;
31*a* . . . window part;
32, 32*a*, 62 . . . bending member;
33 . . . fixed part;
34, 36, 66 . . . sliding part;
34*a*, 36*a* . . . engagement part;
35, 65 . . . linear linking part;
52 . . . accordion-like part;
67 . . . resistance-imparting projection;
AW . . . abdominal wall;
S . . . stomach; SW . . . stomach wall

DETAILED DESCRIPTION OF THE INVENTION

Mode of Embodiment 1

First Embodiment

Figure 1:
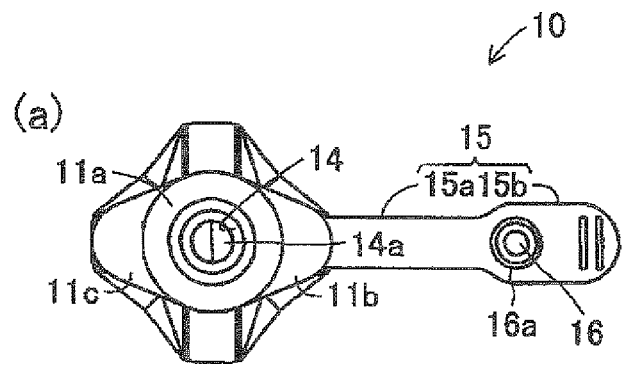
FIG. 1 shows the gastrostomy catheter, where (a) is a plan view, (b) is a front view, and (c) is a bottom view.
Figure 1:
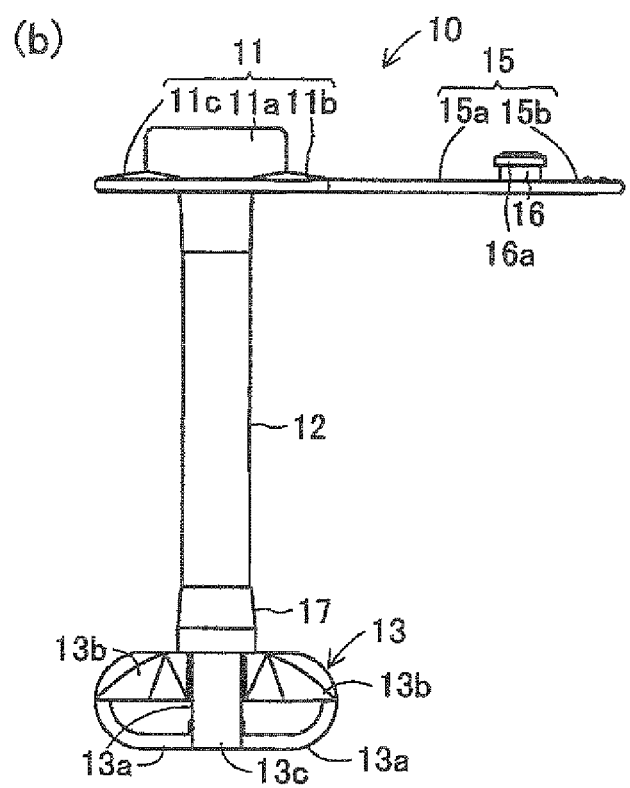
Figure 1:
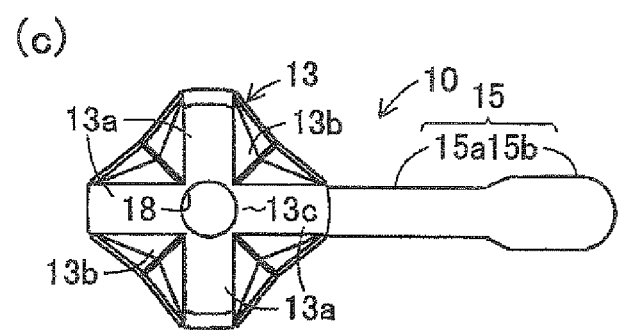
Figure 2:
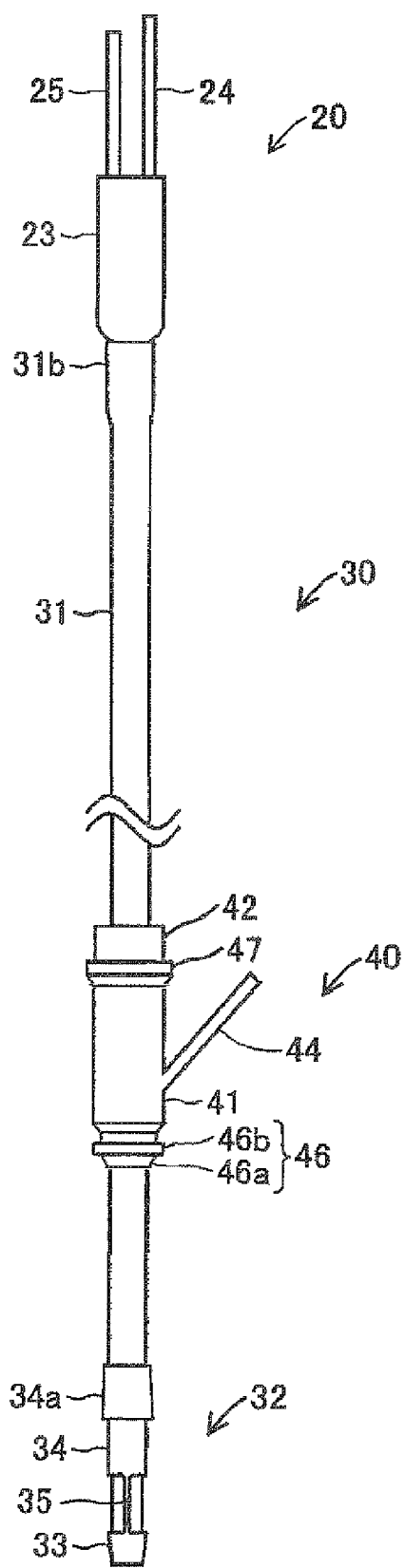
FIG. 2 is a front view showing a state in which the bending instrument for an endoscope according to a first embodiment of the present invention is fitted to a fiberscope.

The first embodiment of the present invention will be described below with reference to the figures. FIG. 1 shows a gastrostomy catheter 10 which is used in this embodiment, and FIG. 2 shows a state in which a bending instrument 30 for an endoscope is fitted to a fibrescope 20 which acts as the endoscope according to the present invention which passes inside the gastrostomy catheter 10. The endoscope set according to the present invention comprises the gastrostomy catheter 10, fibrescope 20 and bending instrument 30 for an endoscope. The gastrostomy catheter 10 comprises an external fixed part 11, a tubular part 12 which is linked to the center of the lower end surface of the external fixed part 11, and an intra-stomach fixed part 13 which is attached to the lower end of the tubular part 12, all these components being made of a soft plastic material such as polyurethane or silicone. In the description that follows, the external fixed part 11 will be taken as the upper side, and the intra-stomach fixed part 13 will be taken as the lower side.

The external fixed part 11 comprises an insertion opening 11*a* which is annular and fairly thick, and projecting pieces 11*b*, 11*c* of which the outline is elliptical and includes the insertion opening 11*a*, these pieces projecting at both sides from the lower end of both side parts of the insertion opening 11*a*, when seen as a plane. The function of these projecting pieces 11*b*, 11*c* is to prevent the gastrostomy catheter 10 from being pulled into the stomach S (see FIGS. 7 to 9). A valve body 14*a* which is formed with a central slit is then provided on the inner peripheral surface of an insertion hole 14 which is formed in the center of the insertion opening 11*a*, passing through vertically. Furthermore, an engagement groove is formed along the circumference at the upper side of the valve body 14*a* on the inner peripheral surface of the insertion hole 14, although this is not depicted. A cover part 15 for closing off the insertion hole 14 of the insertion opening 11*a* is then joined to the tip end of the projecting piece 11*b*.

The cover part 15 comprises an elongate strip-shaped linking part 15*a* which is linked to the tip end part of the projecting piece 11*b*, and a broad part 15*b* which is shorter and wider than the strip-shaped linking part 15*a*, and is formed at the tip end of the strip-shaped linking part 15*a*. A stopper part 16 shaped like a column which is short in the axial direction is then provided on the broad part 15*b*. The strip-shaped linking part 15*a* is flexible, and it can flex so as to vertically rotate, or bend at a sharp angle, with the linking part to the projecting piece 11*b* at the center. The stopper part 16 is provided on the strip-shaped linking part 15*a* side portion of the broad part 15*b*, so as to face the insertion hole 14 when the strip-shaped linking part 15*a* is bent to position the broad part 15*b* above the insertion opening 11*a*.

The stopper part 16 is formed with a columnar shape which can fit into the insertion hole 14, and it is provided on its outer peripheral surface with an annular projection 16*a* running along its periphery, this projection being able to detachably engage with the engagement groove formed on the inner peripheral surface of the insertion hole 14. Accordingly, it is possible to engage the engagement groove with the annular projection 16*a* by bending the strip-shaped linking part 15*a* so that it is upwardly inverted, and pushing the stopper part 16 into the insertion hole 14, and this makes it possible to close off the insertion hole 14 of the insertion opening 11*a* in an airtight and liquid-tight manner. It is also possible to open the insertion hole 14 of the insertion opening 11*a* by pulling the broad part 15*b* to release the fitting between the stopper part 16 and the insertion hole 14.

The tubular part 12 is formed as a cylindrical shape, and a through-hole 12*a* (see FIG. 12) for allowing the passage of fluids such as nutrients and food in fluid form is formed inside it; the upper end of the through-hole 12*a* links in communication with the insertion hole 14 of the external fixed part 11. The intra-stomach fixed part 13 is connected to the tubular part 12 via a connection part 17 which is fixed to the lower end of the tubular part 12. The connection part 17 is formed as a cylinder for covering the outer peripheral surface of the tubular part 12 and is integrally formed with the intra-stomach fixed part 13. The connection part 17 is then fixed to the lower end of the tubular part 12, in a state in which it cannot be removed from the tubular part 12.

The intra-stomach fixed part 13 comprises four strip-shaped linking parts 13*a* which are linked to the edge of a lower end opening of the connection part 17 and extend in four directions, four linking film parts 13*b* which are provided between the upper parts of each of the linking parts 13a and form a roughly dome-shaped stomach wall contact part with the four linking parts 13a, and a converging part 13c where the tip ends of all of the linking parts 13a converge. The four linking parts 13a comprise strip-shaped members which are bent into substantially semi-circular shapes which split into four directions from the lower end of the connection part 17, respectively extending downwards from the horizontal, after which they converge below the central axis of the tubular part 12, linking to form the converging part 13c. That is to say, the converging part 13c allows each of the linking parts 13a to link by joining the lower ends of all of the linking parts 13a, and it is also positioned by all of the linking parts 13a below the central axis of the tubular part 12.

Moreover, the intra-stomach fixed part 13 which comprises the linking parts 13a, linking film parts 13b and the converging part 13c is integrally formed together with the connection part 17. Furthermore, all of the linking parts 13a and linking film parts 13b are made of a soft, flexible, elastic material, and the overall flat roughly spherical shape is normally maintained by means of this elasticity, as shown in FIG. 1, but the shape can be extended to make it straight and elongate by pulling the converging part 13c downwards. Furthermore, the lower end of the through-hole 12a of the tubular part 12 opens between the upper ends of the linking parts 13a.

Further, spaces formed between the lower parts of each of the linking parts 13a form channels for the passage of fluids such as nutrients and food in fluid form sent out from the through-hole 12a of the tubular part 12 into the stomach S. A through-hole 18 is additionally formed in the center of the converging part 13c, and a cylindrical engagement part 18a (see FIG. 12) which acts as the engagement part according to the present invention is formed at the top of said through-hole 18 (converging part 13c). In other words, the through-hole 18 comprises the inner peripheral surface of the cylindrical engagement part 18a, and its diameter is smaller than the diameter of the insertion hole 14 of the external fixed part 11 and the through-hole 12a of the tubular part 12. The intra-stomach fixed part 13 configured in this manner is positioned on the inner surface of the patient's stomach wall SW (see FIGS. 7 to 9) and its function is to prevent the gastrostomy catheter 10 from being removed from the patient's body.

Figure 3:
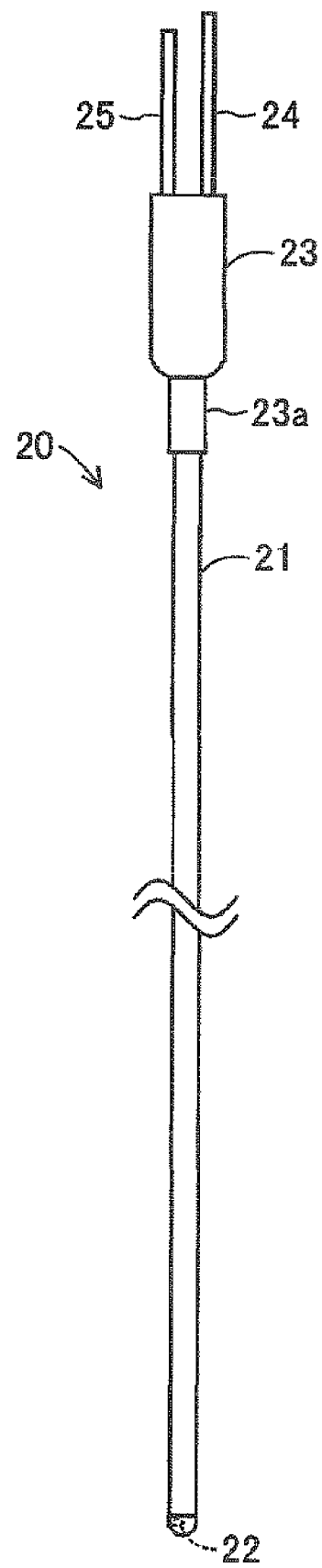
FIG. 3 is a front view showing the fiberscope.

As shown in FIG. 3, the fibrescope 20 has a configuration in which a lens 22 is attached to the tip end of a fibrescope shaft 21 and a connection part 23 is attached to the rear end thereof. The fibrescope shaft 21 is flexible and it is configured by a bundle of fibres comprising a plurality of light guides (not depicted) for irradiating light onto the stomach wall SW, and an image guide (not depicted) for sending reflected light via the lens 22. The connection part 23 is connected to wiring 24 for connecting the image guide to an image display device (not depicted), and wiring 25 for connecting the light guides to a light source device (not depicted).

The lens 22 sends images obtained by light irradiation to the image display device, via the image guide and the wiring 24. In other words, the light guides irradiate the inner surface of the stomach wall SW with light sent from the light source device to make observation possible, and the image guide sends the light which is reflected from the inner surface of the stomach wall SW and focused by means of the lens 22 to the image display device. The image display device then enlarges the images based on the reflected light sent and displays them on an image display part provided in the image display device.

Figure 4:
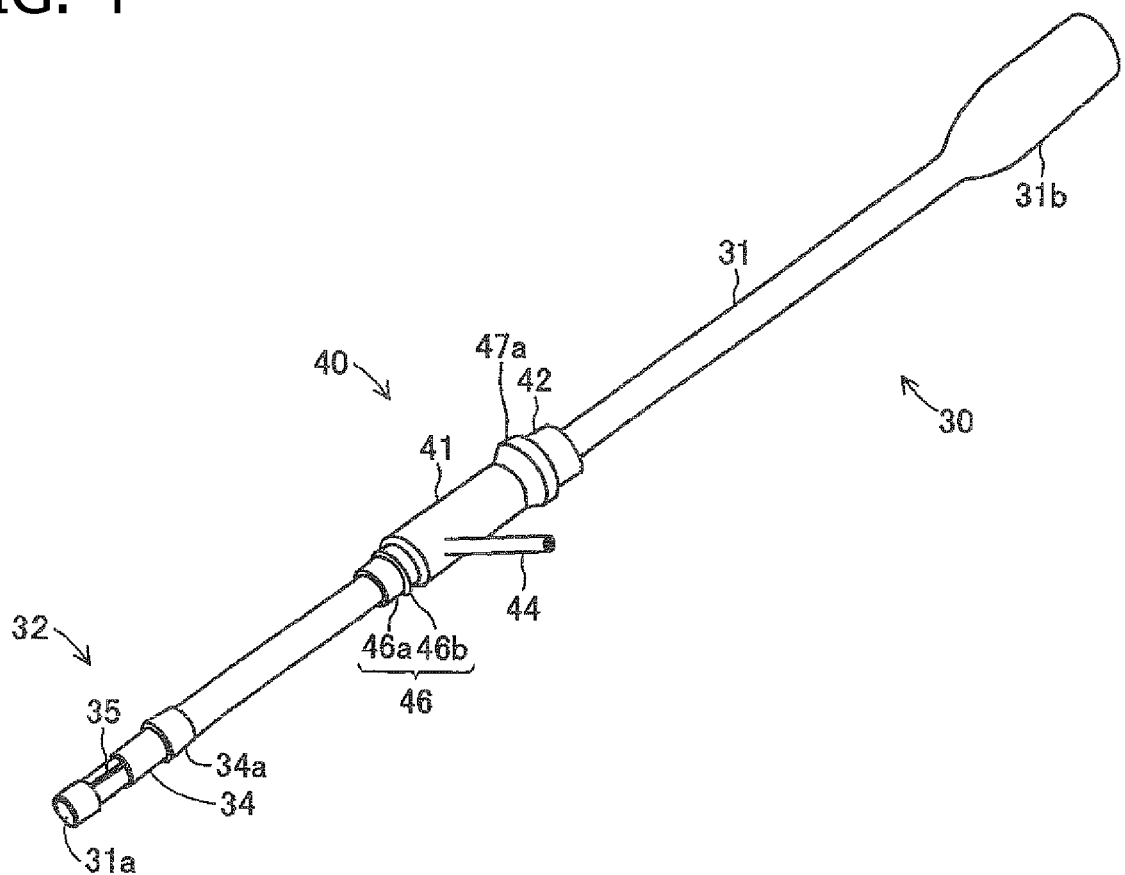
FIG. 4 is an oblique view showing a state in which the insertion aid is fitted to the bending instrument for an endoscope.

The bending instrument 30 for an endoscope covers the fibrescope shaft 21 of the fibrescope 20 so as to prevent the fibrescope shaft 21 from becoming soiled, and is also used to change the direction of observation of the fibrescope 20, by bending the tip end portion of the fibrescope shaft 21. The bending instrument 30 for an endoscope comprises the sheath 31 and the bending member 32 shown in FIG. 4.

The sheath 31 is flexible and comprises a tube which is closed off by a window part 31a wherein the tip end is light-transmissive, and in which the base end part 31b on the opening side is somewhat greater in diameter than the other portion. Said sheath 31 is formed to have a thickness which allows it to cover the fibrescope shaft 21, and it is fitted to the fibrescope shaft 21 by pushing the narrow-diameter part 23a at the tip end of the connection part 23 into the base end part 31b. In this case, the sheath 31 is removed from the fibrescope shaft 21 using a member such as a clamp, a fastening tool or a clasping tool. In this state, a configuration is adopted in which the lens 22 is in contact with the inner surface of the window part 31a. Furthermore, the surface of the window part 31a is formed as a projecting curved surface which projects downwards.

Figure 5:
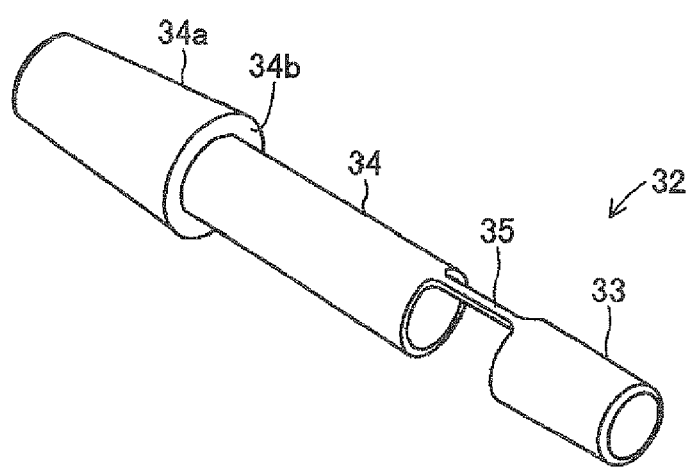
FIG. 5 is an oblique view showing the bending member.

As shown in FIG. 5, the bending member 32 comprises a cylindrical fixed part 33, a cylindrical stepped sliding part 34 which is longer in the axial direction than the fixed part 33, and a linear linking part 35 which acts as the linking part according to the present invention and links the fixed part 33 and the sliding part 34. The fixed part 33 comprises a cylindrical body in which the diameter of the lower portion tapers to become somewhat smaller than the diameter of the upper portion. The inner diameter of the upper portion of the fixed part 33 is somewhat greater than the outer diameter of the sheath 31, and the inner diameter of the lower end part of the fixed part 33 is somewhat smaller than the outer diameter of the sheath 31. Furthermore, the outer diameter of the upper portion of the fixed part 33 is smaller than the diameter of the through-hole 18 of the intra-stomach fixed part 13.

Consequently, the fixed part 33 can penetrate into the gastrostomy catheter 10 from the insertion hole 14 towards the through-hole 18. Furthermore, when the sheath 31 is inserted into the fixed part 33 from the upper part towards the lower part from the tip end side, the outer periphery of the tip end of the sheath 31 abuts the inner periphery at the lower end of the fixed part 33. Consequently, the sheath 31 cannot pass through inside the fixed part 33 and it is in a state in which it covers the fibrescope shaft 21. Moreover, when the bending instrument 30 for an endoscope is being used, the fixed part 33 is fixed to the outer periphery of the tip end of the sheath 31 by means of adhesive.

The inner diameter of the sliding part 34 is somewhat greater than the outer diameter of the sheath 31, and when the sheath 31 passes through the sliding part 34, the sliding part 34 is able to slide along in the length direction of the sheath 31. Furthermore, a latch part 34a which has a greater diameter than the lower portion of the sliding part 34 is formed at the upper part of the sliding part 34. Said latch part 34a is formed with a shape which tapers upwards in which the outer diameter at the upper portion is smaller than the outer diameter at the lower portion. A step part 34b having a horizontal surface is then formed at the lower end of the latch part 34a.

The outer diameter of said step part 34b is smaller than the diameter of the insertion hole 14 of the external fixed part 11 and of the through-hole 12a of the tubular part 12, but greater than the diameter of the through-hole 18 of the intra-stomach fixed part 13. Consequently, when the bending member 32 is inserted into the gastrostomy catheter 10 from the insertion hole 14 towards the through-hole 18, the bending member 32 passes through the insertion hole 14 of the external fixed part 11 and the through-hole 12a of the tubular part 12. The lower portion of the sliding part 34 then also passes through the insertion hole 18 of the intra-stomach fixed part 13, but when the step part 34b reaches the cylindrical engagement part 18a, the step part 34b and the cylindrical engagement part 18a engage, and the engagement part 34a cannot pass through the through-hole 18.

Furthermore, the linear linking part 35 is flexible and links the upper end edge of the fixed part 33 and the portion opposite at the lower end edge of the sliding part 34. After the fibrescope shaft 21 of the fibrescope 20 has passed inside the bending member 32 together with the sheath 31, and the outer periphery of the tip end of the sheath 31 has engaged with the inner periphery at the lower end of the fixed part 33, when the sheath 31 etc. are inserted, the direction in which the tip end of the fibrescope 20 is oriented can be changed by bending this linear linking part 35. In this case, the linear linking part 35 is positioned on the inner peripheral side when the fibrescope shaft 21 etc. is bent, and it keeps the distance between the upper end edge of the fixed part 33 and the lower end edge of the sliding part 34 substantially constant.

Figure 6:
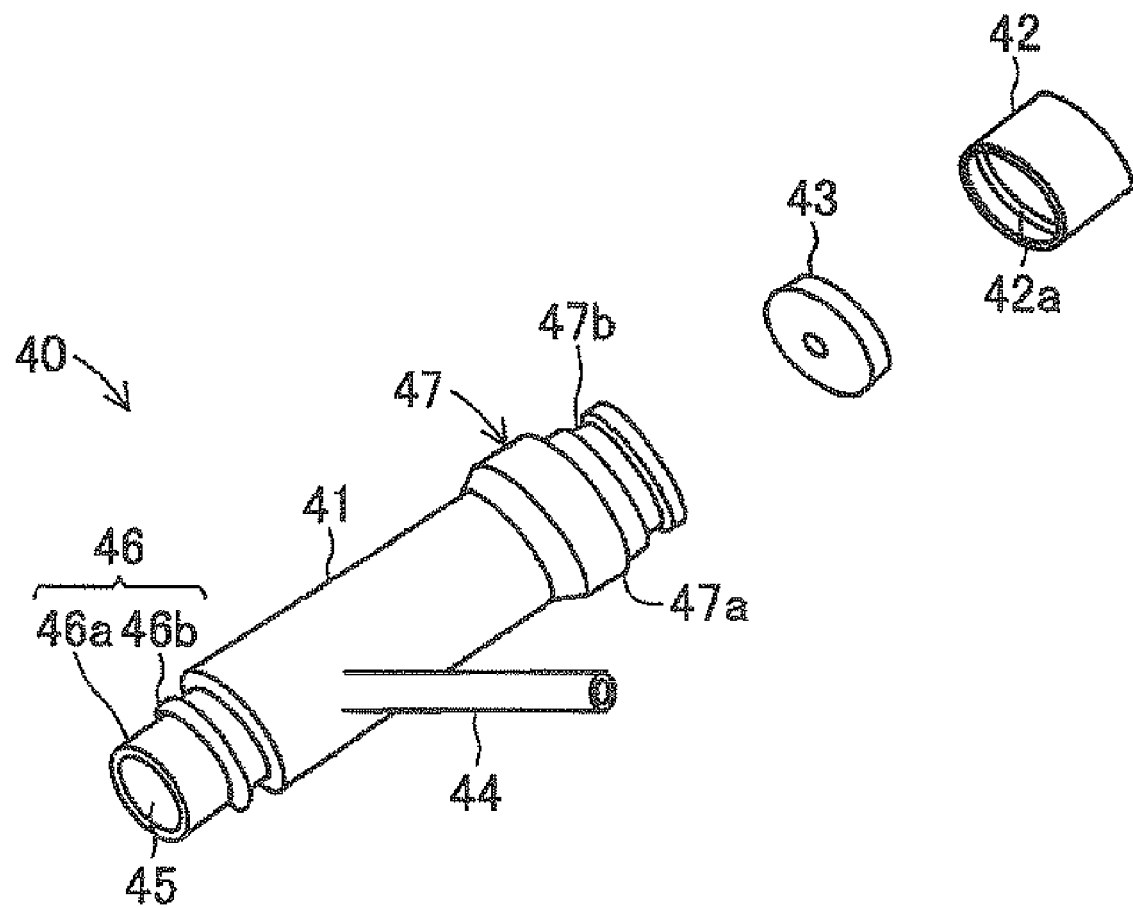
FIG. 6 is an oblique exploded view showing the insertion aid.

The bending instrument 30 for an endoscope configured in the manner described above passes inside the gastrostomy catheter 10 using an insertion aid 40. The insertion aid 40 is an instrument which is fitted to the gastrostomy catheter 10 for smoothing the passage of the fibrescope 20 etc. through the gastrostomy catheter 10, and it comprises a cylindrical main body 41, a valve restraining member 42, a sealing member 43, and a branch pipe 44 which branches off from the cylindrical main body 41, as shown in FIG. 6. The cylindrical main body 41 is formed as an elongate cylinder in which is formed a through-hole 45 which allows the fibrescope shaft 21 together with the sheath 31 to pass therein. Furthermore, a connection part 46 is formed at the lower end of the cylindrical main body 41, and an insertion opening 47 is formed at the upper end of the cylindrical main body 41.

The connection part 46 has a configuration in which an engaging protrusion 46b is formed around the circumference in substantially the center in the axial direction of a cylindrical connection part main body 46a which is formed to have a narrower diameter than the central portion of the cylindrical main body 41. The connection part main body 46a has a cylindrical shape of which the diameter is somewhat smaller than the diameter of the insertion hole 14 of the gastrostomy catheter 10, and the engaging protrusion 46b is of a size so that it can engage with the engagement groove inside the insertion hole 14 of the gastrostomy catheter 10. Moreover, when the engaging protrusion 46b has engaged with the engagement groove, the area between the connection part 46 and the inner peripheral surface of the insertion hole 14 are configured to achieve an airtight and liquid-tight state. Furthermore, at this time the lower end of the connection part 46 pushes open a slit in the valve body 14a which is formed in the insertion hole 14, and the outer peripheral surface of the connection part main body 46a and the peripheral edge of the slit achieve a state of close attachment.

The insertion opening 47 is formed to have a larger diameter than the central portion of the cylindrical main body 41, and a flange-like engagement part 47a is formed at the lower portion thereof. Furthermore, an annular engaging recess 47b is formed at the upper portion of the engagement part 47a on the outer peripheral surface of the insertion opening 47. The branch pipe 44 is formed with a cylindrical shape extending obliquely upwards at an inclination of approximately 45° to the cylindrical main body 41 from the upper side of the connection part 46 of the cylindrical main body 41, and it has a narrower diameter than the cylindrical main body 41. An air supply device (not depicted) is connected to the tip end of said branch pipe 44, and air supplied from the air supply device passes through the inside of the branch pipe 44 and is sent into the cylindrical main body 41. Furthermore, a configuration is adopted in which an airflow channel (not depicted) for the passage of air is formed between the inside of the cylindrical main body 41 and the lower end inside the connection part 46, and air which is sent to the lower end inside the cylindrical main body 41 is discharged to the outside from the lower end of the connection part 46.

The valve restraining member 42 comprises a cap-like body formed with a hole (not depicted) which has substantially the same diameter as the through-hole 45 of the cylindrical main body 41, and an engaging protrusion 42a which can engage with the engaging recess 47b is formed along the circumference on the inner peripheral surface thereof. Said engaging protrusion 42a can go over the upper portion of the insertion opening 47 to engage with the engaging recess 47b, by pushing the lower-end opening side of the valve restraining member 42 onto the insertion opening 47 of the cylindrical main body 41.

The sealing member 43 comprises a deformable annular elastomer, such as natural rubber, synthetic rubber or silicone. The inner diameter of this sealing member 43 is somewhat smaller than the inner diameter of the through-hole 45, and the outer diameter of the sealing member 43 is substantially the same as the outer diameter of the upper end surface of the insertion opening 47. The insertion aid 40 is assembled by placing the sealing member 43 at the upper end surface of the cylindrical main body 41, and engaging the engaging protrusion 42a of the valve restraining member 42 with the engaging recess 47b of the cylindrical main body 41. At this time, the sealing member 43 is flattened, and the flattened portion projects to the inner peripheral side. Consequently, when the insertion aid 40 is fitted to the fibrescope shaft 21 which is covered by the sheath 31, the area between the sealing member 43 and the sheath 31 is in close contact so as to be liquid-tight and airtight.

Figure 7:
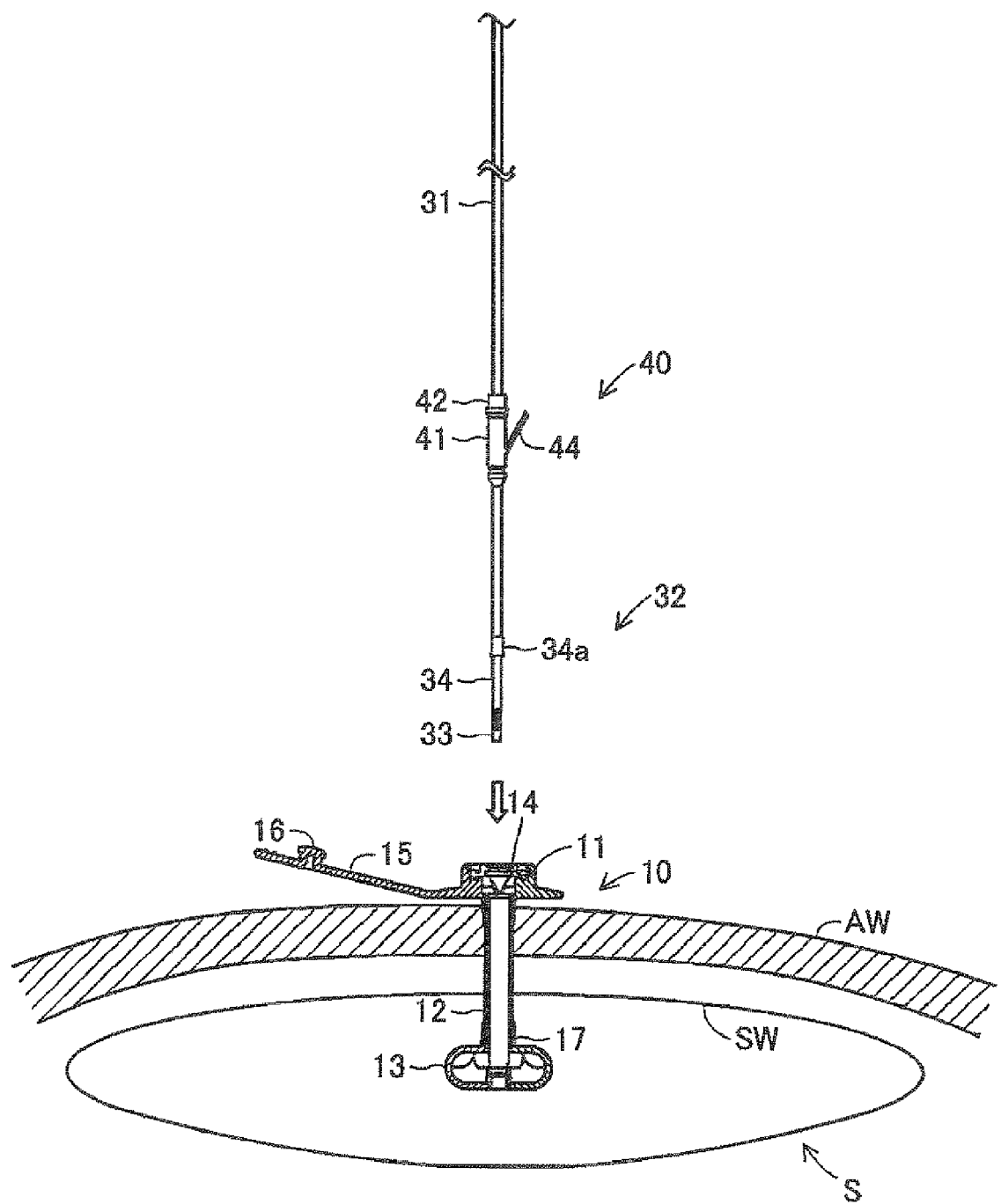
FIG. 7 is a partial cutaway view in cross section showing a state in which the fiberscope to which the bending instrument for an endoscope is fitted is positioned above the gastrostomy catheter which is indwelling in the patient.

A description will be given next, with reference to FIGS. 7 to 9, of the method of confirming the indwelling position of the gastrostomy catheter 10 using the bending instrument 30 for an endoscope and the insertion aid 40 configured in the manner described above. FIG. 7 shows a state in which the gastrostomy catheter 10 is indwelling in a gastrostomy hole provided in the abdominal wall AW and the stomach wall SW of a patient, where said gastrostomy catheter 10 is made indwelling in the gastrostomy hole using a specific instrument for fitting it. A description of the structure of this fitting instrument and the method used to make the catheter indwelling will be omitted here. In the state shown in FIG. 7, the stopper part 16 of the gastrostomy catheter 10 is removed from the insertion hole 14 to open the upper end of the insertion hole 14.

Furthermore, the fiberscope 20 to which the sheath 31, the bending member 32 and the insertion aid 40 are fitted is positioned above the gastrostomy catheter 10. The fibrescope 20 etc. which is in this state is moved down in the direction of the arrow shown in the figures so that the fibrescope shaft 21 projecting from the lower end of the insertion aid 40 is inserted into the insertion hole 14 of the gastrostomy catheter 10 together with the sheath 31 and the bending member 32. At this time, an operator holds both sides of the insertion opening 11a on the gastrostomy catheter 10 where the projecting pieces 11b, 11c are not formed with one hand, and holds the insertion aid 40 with the other hand, and pushes the insertion aid 40 into the gastrostomy catheter 10.

Figure 8:
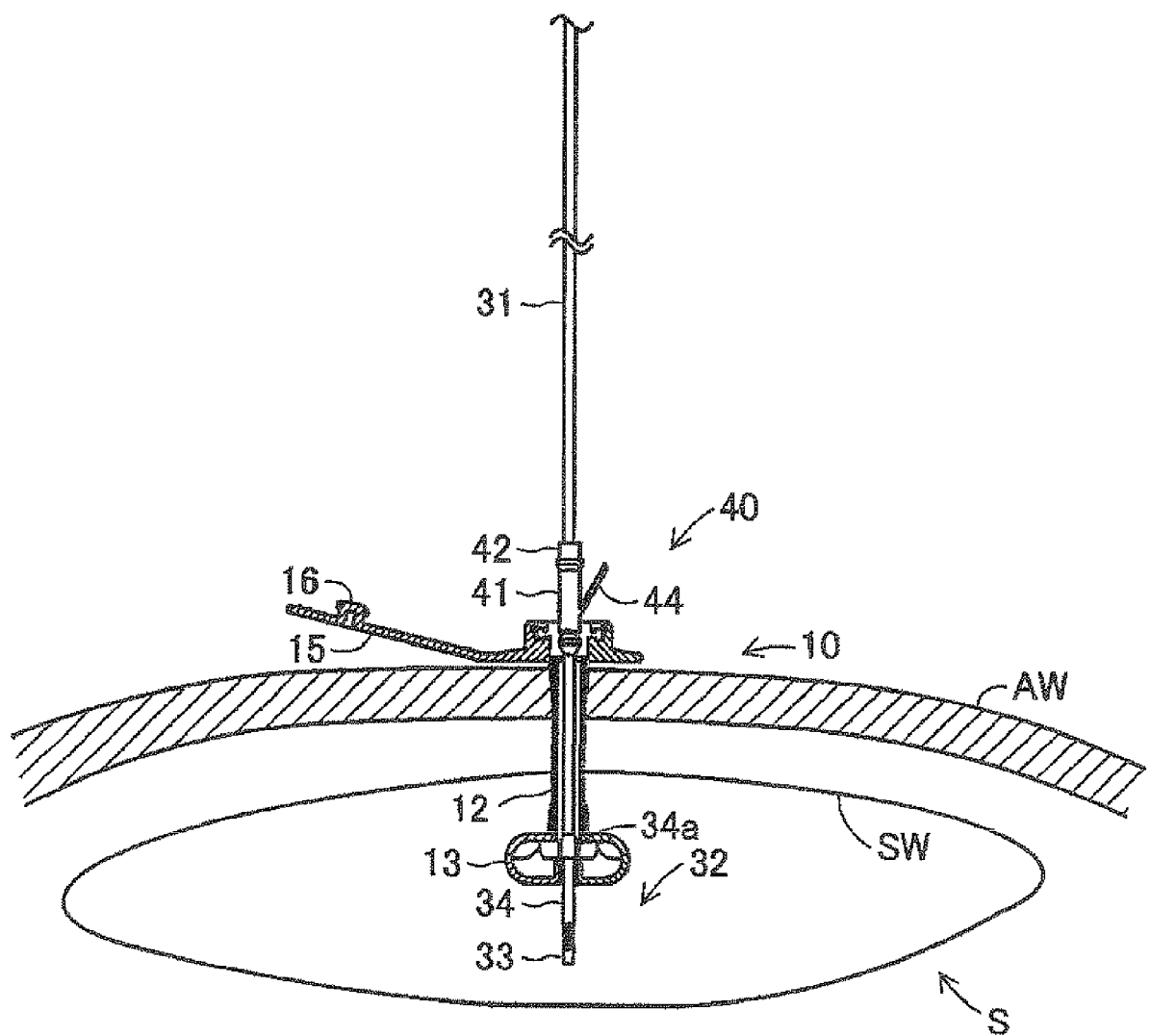
FIG. 8 is a partial cutaway view in cross section showing a state in which the fiberscope to which the bending instrument for an endoscope is fitted is inserted into the gastrostomy catheter which is indwelling in the patient.

As shown in FIG. 8, this makes it possible to engage the insertion aid 40 with the gastrostomy catheter 10. The engagement in this case is brought about by the engagement of the engaging protrusion 46b of the insertion aid 40 with the engagement groove of the gastrostomy catheter 10, and a state of air-tightness is achieved between the insertion aid 40 and the gastrostomy catheter 10. The fibrescope 20 is then further inserted towards the lower side of the gastrostomy catheter 10 together with the sheath 31 and the bending member 32, and the lower portion of the fibrescope shaft 21, sheath 31 and bending member 32 project downwards from the through-hole 18 formed at the lower end of the gastrostomy catheter 10. It should be noted that the fibrescope shaft 21 and the bending instrument 30 for an endoscope may pass inside the insertion aid 40 after insertion aid 40 has been connected to the gastrostomy catheter 10.

Next, air is supplied from the air supply device to inside the branch pipe 44, and this air is sent into the stomach S from the connection part 46 via the tubular part 12 of the gastrostomy catheter 10. This allows the stomach S to expand, as shown in FIG. 9. In this case, the area between the gastrostomy catheter 10 and the insertion aid 40, and the area between the insertion aid 40 and the sheath 31 are closed off, respectively, and therefore air inside the stomach S does not leak to the outside. In this state, light is generated by means of the light source device, whereby light passes through the wiring 25 and the light guides of the fibrescope shaft 21, and is irradiated towards the stomach wall SW. Furthermore, in this case, the fibrescope 20 and the sheath 31 etc. are pushed into the body as required, whereby, as shown in FIG. 9, the lower portion of the fibrescope shaft 21 bends together with the sheath 31 so that it is possible to change the position of irradiation of the stomach wall SW by the light guides.

Figure 9:
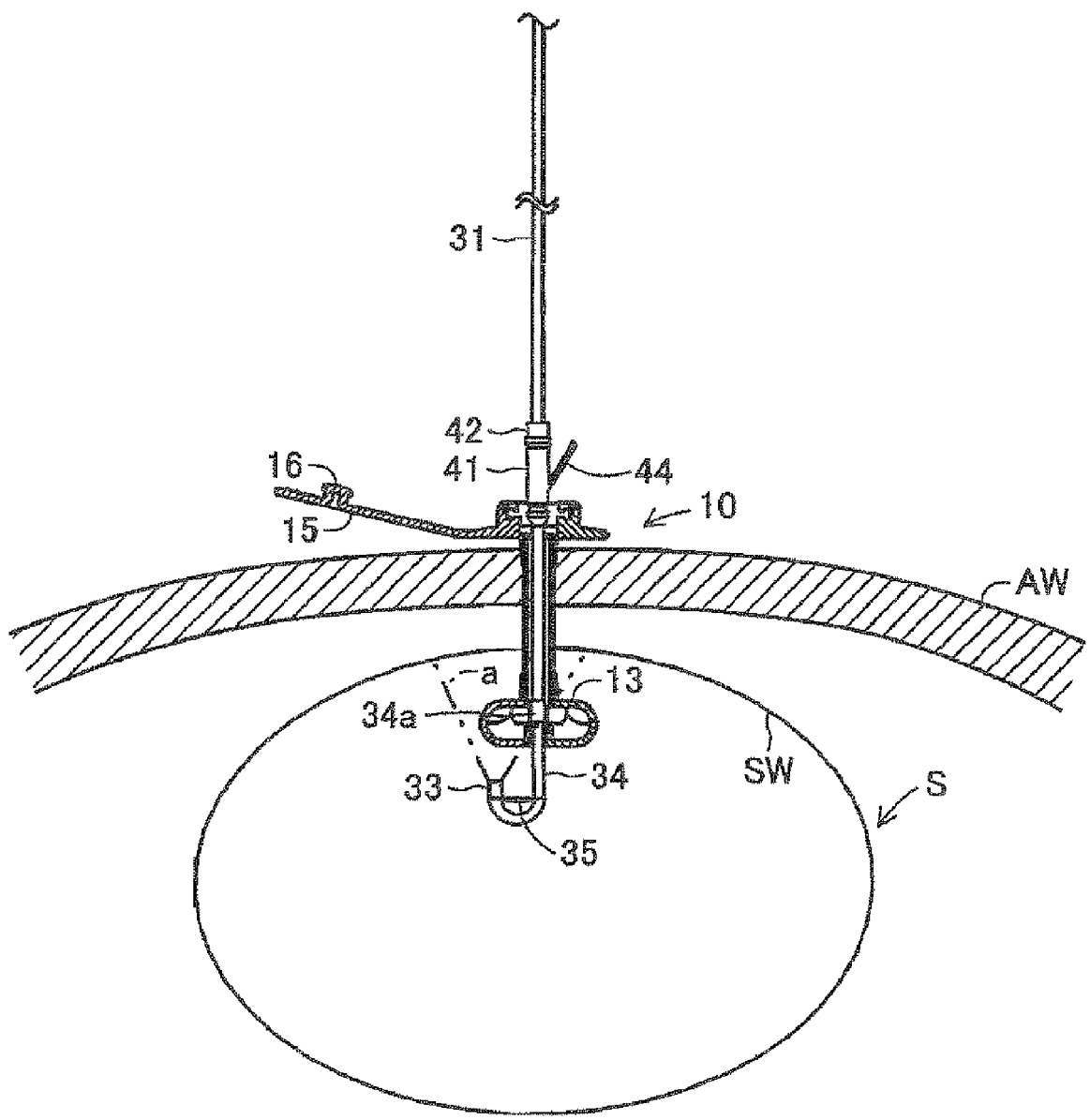
FIG. 9 is a partial cutaway view in cross section showing a state in which the indwelling position of the gastrostomy catheter is confirmed using the fiberscope.
Figure 10:
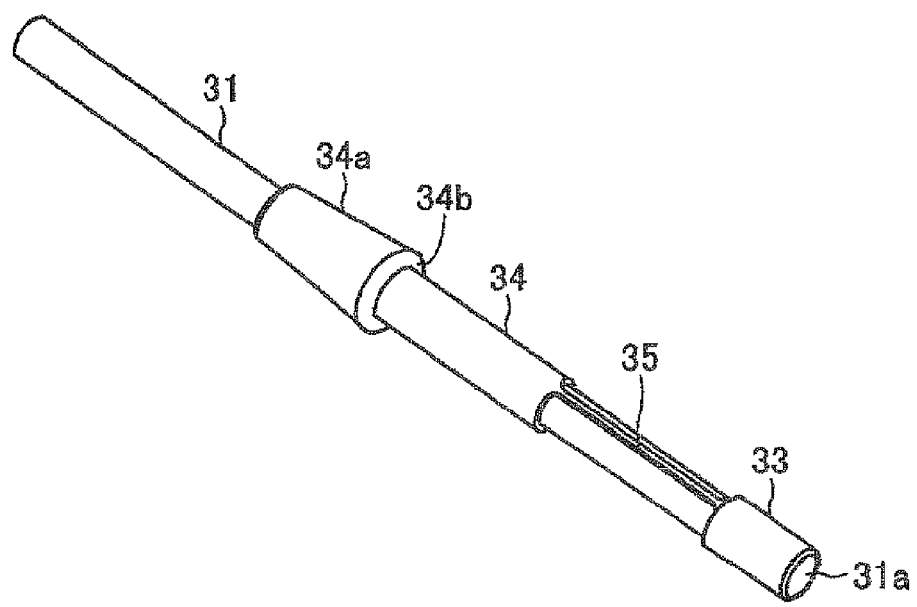
FIG. 10 is an enlarged partial view of the state shown in FIG. 8 showing the fiberscope to which the bending instrument for an endoscope is fitted.
Figure 11:
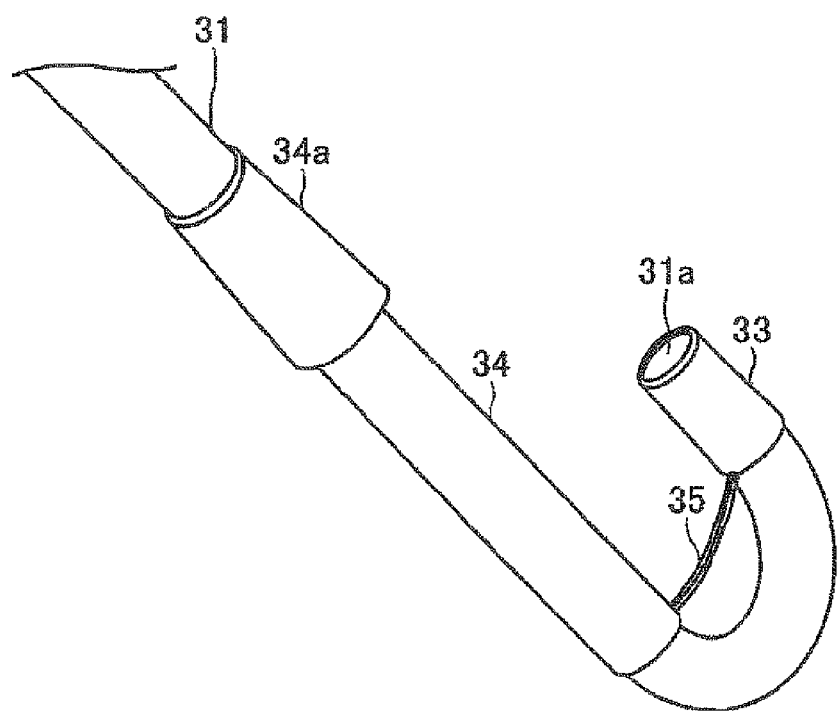
FIG. 11 is an enlarged partial view of the state shown in FIG. 9 showing the fiberscope to which the bending instrument for an endoscope is fitted.
Figure 12:
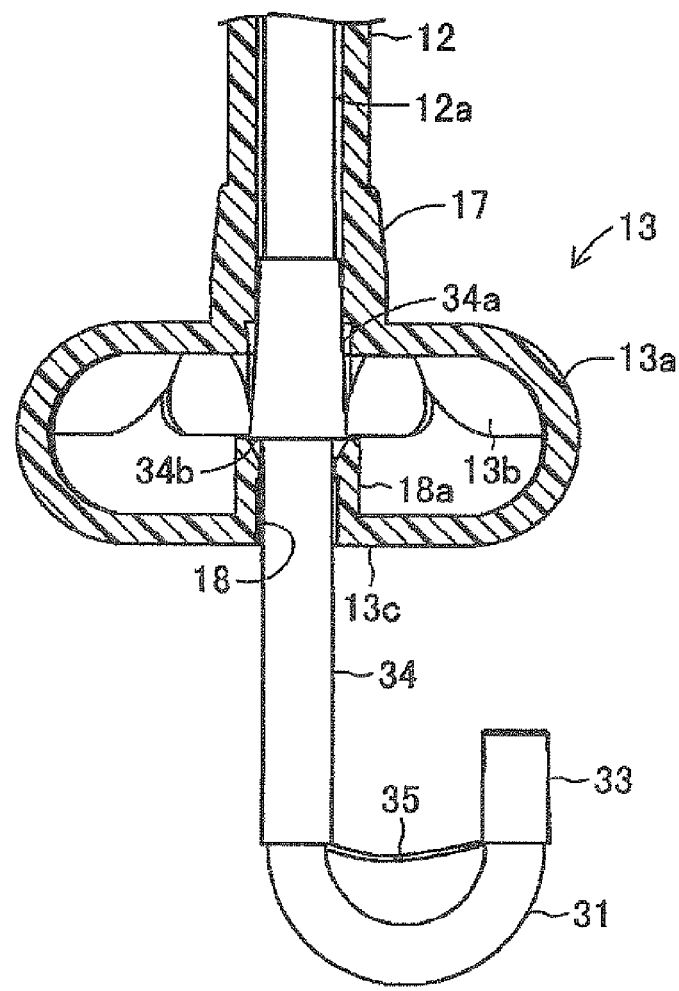
FIG. 12 is an enlarged partial view showing a state in which the bending instrument for an endoscope shown in FIG. 11 is engaged with the cylindrical engagement part of the intra-stomach fixed part.

In the state shown in FIG. 8, the fibrescope shaft 21, sheath 31 and bending member 32 extend straight ahead, as shown in FIG. 10. Further, when more pressure is applied to the bending member 32 via the fibrescope 20 and the sheath 31 to reach the state shown in FIG. 9, the fibrescope shaft 21, sheath 31 and bending member 32 are at the state shown in FIG. 11. That is to say, from the state shown in FIG. 8, when the bending member 32 is pushed via the fibrescope shaft 21 and the sheath 31, the fixed part 33 of the bending member 32 and the lower portion of the sliding part 34 pass through the through-hole 18 of the intra-stomach fixed part 13 and enter the stomach S, but the engagement part 34a of the sliding part 34 engages with the cylindrical engagement part 18a of the through-hole 18 and is held in the intra-stomach fixed part, as shown in FIG. 12.

Consequently, the fixed part 33 moves so as to describe the arc of a circle, with the linear linking part 35 as the radius, and the tip end portion of the fibrescope shaft 21 and the sheath 31 follow this movement of the fixed part 33 while bending, and protrude inside the stomach S. The range shown by the two-dot chain line a in FIG. 9 shows the range of light irradiation by the light guides. Light which is irradiated by means of the light guides and reflected off the stomach wall SW is focused by the lens 22, after which it is sent to the image display device by way of the image guide and the wiring 24 of the fibrescope shaft 21.

Images which are sent to the image display device are enlarged in the image display part of the image display device and displayed, and therefore it is possible to confirm whether or not the intra-stomach fixed part 13 of the gastrostomy catheter 10 is positioned in the correct state inside the stomach S, from the images displayed in said image display part. If it is possible to confirm that the gastrostomy catheter 10 is indwelling in the correct state, an operation is carried out in which the fibrescope 20 is removed from the gastrostomy catheter 10 together with the sheath 31, bending member 32 and insertion aid 40, and also the sheath 31 and the bending member 32 are removed from the fibrescope shaft 21.

In this operation, the fibrescope 20 is first of all pulled slightly upwards together with the bending instrument 30 for an endoscope, and then in the state shown in FIG. 8, the engagement between the engaging protrusion 46b of the insertion aid 40 and the engagement groove of the gastrostomy catheter 10 is released. The fibrescope 20 is then removed from the gastrostomy catheter 10 by pulling it upwards together with the bending instrument 30 for an endoscope and the insertion aid 40. In addition, the insertion aid 40 is removed from the sheath 31, after which the fibrescope shaft 21 is pulled out of the sheath 31. The bending instrument 30 for an endoscope is then disposed of, and the fibrescope 20 can be reused next time.

At this time, the fibrescope shaft 21 and the lens 22 of the fibrescope 20 do not come into contact with the liquids and residues inside the patient's body and stomach S, so they are not soiled and there is no need for the most part to clean or sterilize them. Furthermore, when the fibrescope 20 is reused, a new bending instrument 30 for an endoscope is used. Moreover, in the operation described above, the engagement between the engaging protrusion 46b of the insertion aid 40 and the engagement groove of the gastrostomy catheter 10 is released, and the fibrescope 20 is removed from the gastrostomy catheter 10 together with the bending instrument 30 for an endoscope and the insertion aid 40, but it is also possible to remove the fibrescope 20 etc. from the insertion aid 40, and then to release the engagement between the engaging protrusion 46b of the insertion aid 40 and the engagement groove of the gastrostomy catheter 10.

Furthermore, when nutrient fluid is supplied to the patient's stomach S, for example, by way of the gastrostomy catheter 10 which is indwelling in the patient's body, a connector for a tube extending from a container housing the nutrients is connected to the insertion hole 14 of the gastrostomy catheter 10. In this state, nutrients are supplied to the patient by way of the tube and the gastrostomy catheter 10. At this time, nutrients coming out of the tubular part 12 pass from the intra-stomach fixed part 13 through each of the linking parts 13a, and enter the stomach S. Furthermore, after use, the tube from the container of nutrients is removed from the insertion hole 14 of the gastrostomy catheter 10, and the insertion hole 14 is closed using the stopper part 16. Then, when it becomes necessary to replace the gastrostomy catheter 10 after regular periods of use, it can be replaced with a new gastrostomy catheter 10. In this case also, the indwelling position of the gastrostomy catheter 10 can be confirmed using the fibrescope 20, bending instrument 30 for an endoscope and insertion aid 40 which have been described above.

In this way, the bending instrument 30 for an endoscope according to this embodiment comprises a sheath 31 which can cover the whole of the fibrescope shaft 21 of the fibrescope 20 which is inserted into the patient's body, and a bending member 32 which causes the sheath 31 to bend. The tip end of the sheath 31 facing the lens 22 which is provided at the tip end of the fibrescope shaft 21 comprises a light-transmissive window part 31a. Consequently, there is no reduction in the accuracy of observations made using the fibrescope 20 caused by the sheath 31. Furthermore, the bending member 32 comprises the fixed part 33, the sliding part 34, and the linear linking part 35 which links the fixed part 33 and the sliding part 34, and a latch part 34a which engages with the cylindrical engagement part 18a of the intra-stomach fixed part 13 so as not to allow the sliding part 34 to pass through the intra-stomach fixed part 13 is additionally formed at the upper part of said sliding part.

Accordingly, when the fibrescope shaft 21 which is covered by the sheath 31 is inserted into the gastrostomy catheter 10 and the sliding part 34 of the bending member 32 reaches the cylindrical engagement part 18a of the intra-stomach fixed part 13, the latch part 34a of the sliding part 34 engages with the cylindrical engagement part 18a. After this, when the fibrescope 20 is pushed further into the gastrostomy catheter 10 together with the sheath 31 etc., the fibrescope shaft 21 protrudes outwards at the tip end of the gastrostomy catheter 10 while bending together with the sheath 31.

Consequently, the tip end of the fibrescope shaft 21 can be oriented in any direction by rotating the fibrescope 20 in the axial direction together with the sheath 31 etc., and by adjusting the length of insertion of the fibrescope 20. By means of this, it is possible to change the direction of observation of the fibrescope 20 using a simple operation, enabling more reliable checking of the state of the stomach's inner walls, and more reliable confirmation of the indwelling position of the gastrostomy catheter. Furthermore, the fibrescope 20 is bent using the bending member 32, and therefore it is possible to adopt a simple structure in which the fibrescope 20 does not comprise a mechanism for bending itself. By means of this, it is possible to reduce the components of the endoscope which might fail.

Furthermore, once the inner walls of the stomach S have been checked and the indwelling position of the gastrostomy catheter 10 has been confirmed, the bending instrument 30 for an endoscope is pulled out from the gastrostomy catheter 10 together with the fibrescope 20, after which the fibrescope 20 can be removed from the patient's body without being soiled by gastric juices or the like, by pulling out the fibrescope shaft 21 from the sheath 31 of the bending instrument 30 for an endoscope. As a result, there is almost no need to sterilize or clean the fibrescope 20, which makes sterilizing and cleaning costs almost unnecessary, and also the lifespan of the fibrescope 20 is extended.

Variant Example

Figure 13:
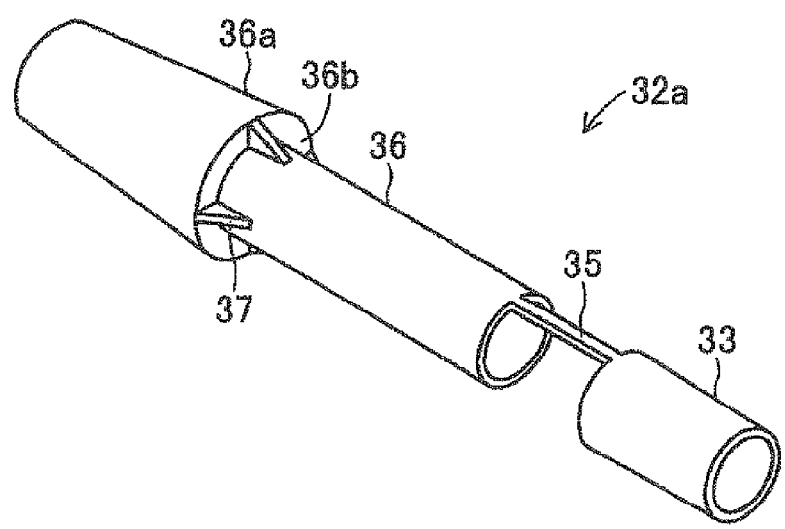
FIG. 13 is an oblique view showing the bending instrument for an endoscope according to a variant example.

FIG. 13 shows a bending member 32a according to a variant example of the first embodiment described above. With this bending member 32a, four ribs 37 at constant intervals are formed on a step part 36b between the lower portion of a sliding part 36 which is formed with a stepped cylindrical shape and the upper part which is a latch part 36a. Each rib 37 is formed as a triangular plate extending obliquely from the lower end of the latch part 36a towards the outer peripheral surface of the lower portion of the sliding part 36.

The configuration of the other components of this bending member 32a is the same as that of the bending member 32 described above. Accordingly, similar components bear similar reference numbers and a description of them will be omitted. With this bending member 32a, strength is improved and also there are no corner parts at the portion which abuts the cylindrical engagement part 18a of the intra-stomach fixed part 13, so the cylindrical engagement part 18a does not get damaged. The other operational effects of this bending member 32a are the same as those of the bending member 32 described above.

Mode of Embodiment 2

Second Embodiment

Figure 14:
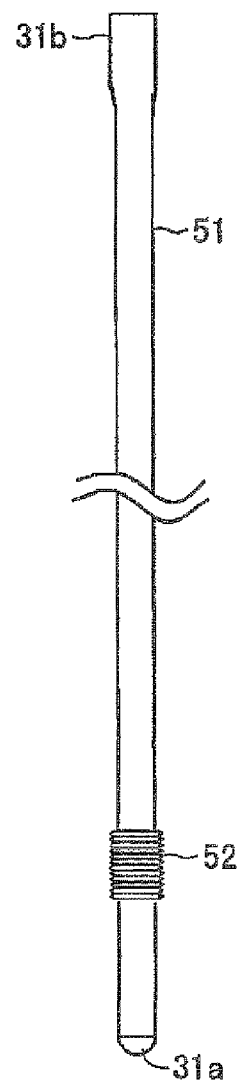
FIG. 14 is a front view showing the sheath for the bending instrument for an endoscope according to a second embodiment.

FIG. 14 shows a sheath 51 for a bending instrument for an endoscope according to the second embodiment of the present invention. With this sheath 51, an accordion-like part 52 comprising a plurality of protrusions which configure the protrusions of the present invention is formed at the lower end portion lying between the fixed part 33 and the sliding part 34 when the abovementioned bending member 32 is fitted. The configuration of the other components of the bending instrument for an endoscope provided with this sheath 51 is the same as that of the bending member 32 described above.

Accordingly, similar components bear similar reference numbers and a description of them will be omitted. This allows the accordion-like part 52 portion of the sheath 51 to bend easily, and makes it possible to prevent folds occurring in the sheath 51. Furthermore, said accordion-like part 52 also acts as the retaining protrusions for preventing the sliding part 34 from being withdrawn from the sheath 51. The other operational effects of the bending instrument for an endoscope provided with this sheath 51 are the same as those of the bending member 32 described above.

Mode of Embodiment 3

The Third Embodiment

Figure 15:
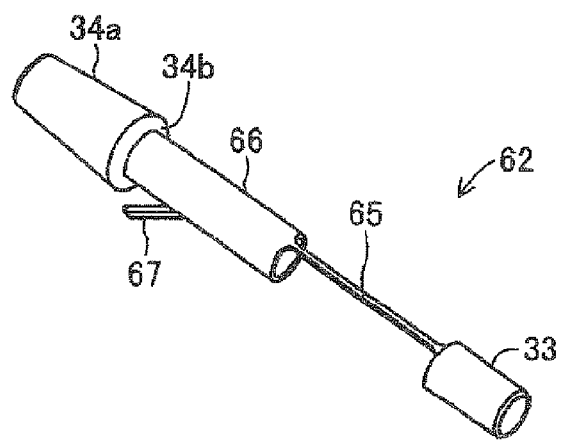
FIG. 15 is an oblique view showing the bending member for the bending instrument for an endoscope according to a third embodiment.

FIG. 15 shows a bending member 62 for a bending instrument for an endoscope according to a third embodiment of the present invention. With this bending member 62, a resistance-imparting projection 67 which is elongate and shaped like a thin board is formed at the tip end portion of a sliding part 66, i.e. the upper part of the narrow diameter portion which constitutes the tip end portion according to the present invention. This resistance-imparting projection 67 extends obliquely towards the base end side of the sliding part 66 from a portion on the opposite side to the portion provided with a linear linking part 65 on the outer peripheral surface of the sliding part 66.

The resistance imparting projection 67 is then pressured at the tip end of the sliding part 66, whereby it simply bends so as to lie along the outer peripheral surface of the sliding part 66, and by applying a fairly large force towards the base end of the sliding part 66 to cause bending of the projection, it bends so as to invert and lie along the outer peripheral surface of the sliding part 66. The configuration of the other components of the bending member 62 provided with this resistance-imparting projection 67 is the same as that of the bending member 32 described above in the first embodiment. Accordingly, similar components bear similar reference numbers in FIG. 15. Furthermore, the configuration of the other components of the bending instrument for an endoscope provided with this bending member 62 is also the same as that of the bending instrument 30 for an endoscope described above in the first embodiment.

Figure 16:
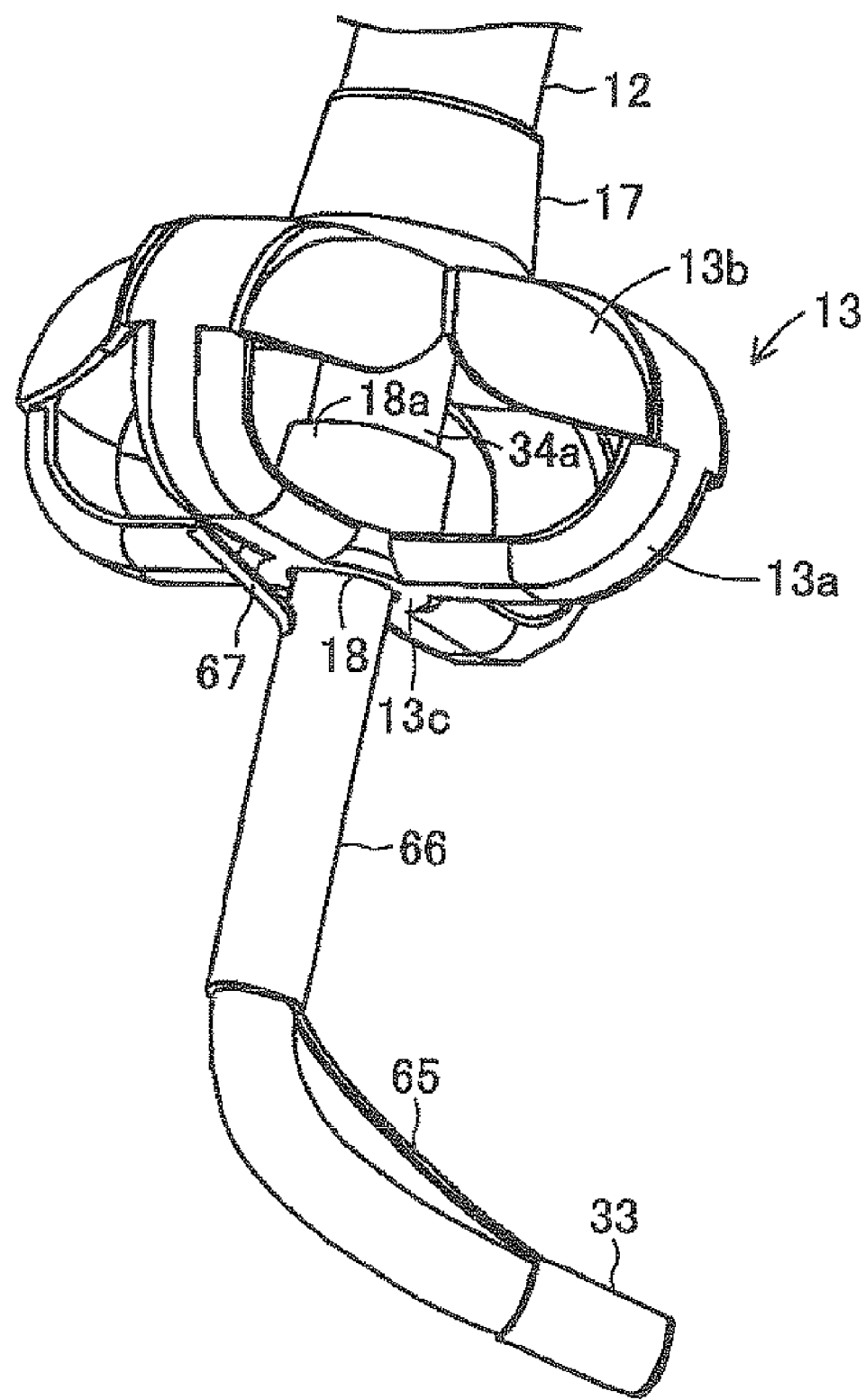
FIG. 16 is an oblique view showing a state in which the tip end of the resistance-imparting projection abuts the intra-stomach fixed part when the fiberscope using the bending member according to the third embodiment starts to be removed from the gastrostomy catheter.

Because of this configuration, when this bending member 62 is used and the fibrescope 20 is pulled slightly upwards together with the sheath 31 and the bending member 62, after the sheath 31 etc. has been put in the state shown in FIG. 9, the bending member 62 reaches the state shown in FIG. 16. In this case, the tip end of the resistance-imparting projection 67 abuts the lower surface of the intra-stomach fixed part 13, and the sliding part 66 is prevented from entering the cylindrical engagement part 18a. Consequently, the fibrescope 20 is pulled upwards together with the sheath 31 with the sliding part 66 still positioned at the lower surface of the intra-stomach fixed part 13. By means of this, the tip end portion of the fibrescope shaft 21 and the sheath 31 arrive at the slightly bent state shown in FIG. 16 from the very bent state shown in FIG. 9.

Figure 17:
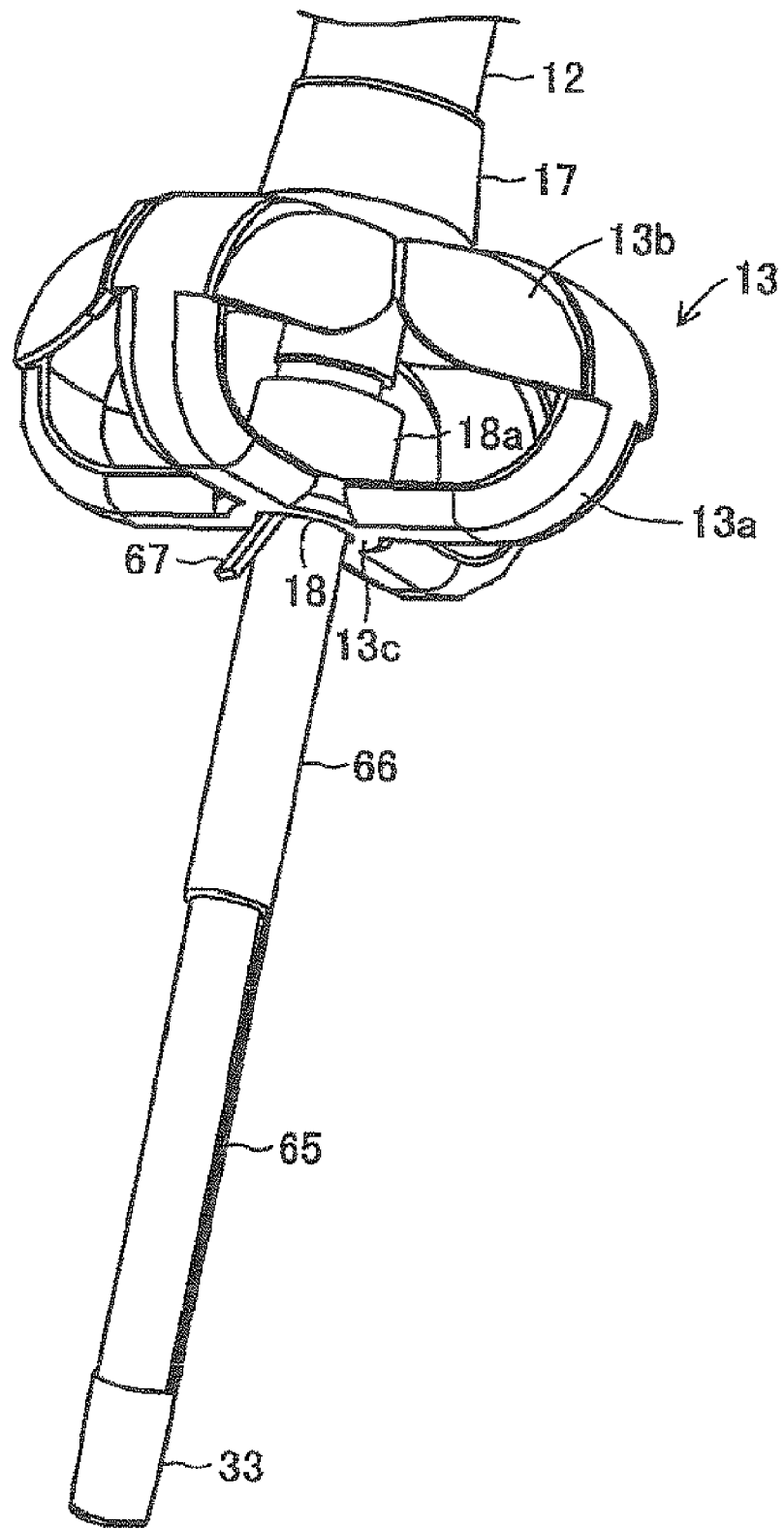
FIG. 17 is an oblique view showing a state in which the base end of the resistance-imparting projection has entered the intra-stomach fixed part when the fiberscope using the bending member according to the third embodiment is being removed from the gastrostomy catheter.

In addition, when the fibrescope 20 is pulled upwards together with the sheath 31 and the bending member 62, the bending member 62 reaches the state shown in FIG. 17. In this state, the tip end portion of the fibrescope shaft 21 and the sheath 31 is substantially in a straight line, and the base end portion of the resistance-imparting projection 67 is entering the cylindrical engagement part 18a. Consequently, when the fibrescope 20 is pulled further upwards together with the sheath 31 and the bending member 62, the resistance-imparting projection 67 enters the cylindrical engagement part 18a, and the sliding part 66 can be withdrawn to the upper part of the cylindrical engagement part 18a.

The fiberscope shaft 21, sheath 31 and bending member 62 are then taken out from the top of the gastrostomy catheter 10. In this way, by virtue of the bending instrument for an endoscope provided with this bending member 62, the operation to remove the fibrescope 20 to which the bending instrument for an endoscope is fitted from the gastrostomy catheter 10 is simplified. The other operational effects of the bending instrument for an endoscope provided with the bending member 62 are the same as those of the bending instrument for an endoscope described above in the first embodiment.

Furthermore, the bending instrument for an endoscope according to the present invention is not limited to the embodiments described above, and appropriate modifications may be implemented within the technical scope of the present invention. For example, in the exemplary embodiments described above, the external fixed part 11 is provided on the gastrostomy catheter 10, but a gastrostomy catheter which is not provided with an external fixed part 11 may also be used. In this case the insertion aid 40 may also be dispensed with. It is also possible to use other devices having similar functions instead of the image display device and light source device etc. In addition, in the second embodiment described above, the accordion-like part 52 is formed on the sheath 51, but a single protrusion around the circumference may be provided instead of the accordion-like part 52. In this case, the protrusion is used as a retaining protrusion for preventing the sliding part 34 from being withdrawn from the sheath 51. Furthermore, when the accordion-like part 52 or a protrusion is provided on the sheath 31 etc., the fixed part of the bending member 32 etc. can be made detachable from the sheath 31 etc. Furthermore, the fixed part 33 may be fixed to the sheath 31 by bonding using heat or flux instead of adhesion.

In one embodiment, the bending instrument for an endoscope according to the present invention configured in the manner described above comprises a sheath which is a separate member and a bending member. Consequently, the sheath can be configured by a member which can cover at least all the parts of the endoscope which are inserted into the body. The tip end of the sheath which faces the tip end of the endoscope comprises a light-transmissive window part, and therefore the sheath causes no reduction in accuracy during observation of the stomach wall or the like using an endoscope. Furthermore, the bending member comprises a fixed part which is attached to the tip end of the sheath, a sliding part which is slidably attached further to the base end side of the sheath than the fixed part, and a linking part which controls the gap between the fixed part and the sliding part so that it does not exceed a specified length.

The sliding part has a structure whereby it can pass through the through-hole of the gastrostomy catheter but engages with the engagement part of the intra-stomach fixed part so as not to be able to go past the intra-stomach fixed part. Moreover, the linking part in this case has a flexible cord shape, thread shape, rod shape or narrow board shape, and links a corresponding part of the fixed part and the sliding part. Accordingly, when the endoscope which is covered by the sheath to which the bending member is attached is inserted into the gastrostomy catheter and the sliding part of the bending member reaches the engagement part of the intra-stomach fixed part, the sliding part engages with the engagement part.

After this, as the endoscope is pushed further into the gastrostomy catheter together with the sheath, progress in the direction of insertion of the tip end of the endoscope and the sheath is controlled by the fixed part so that movement is possible together with the fixed member only in an arcuate direction, taking the length of the linking part as the radius. Furthermore, the portion of the endoscope and the sheath further to the base end side than the tip end is pushed outwards at the tip end of the gastrostomy catheter, and therefore the endoscope projects outwards at the tip end of the gastrostomy catheter while bending together with the sheath. In other words, this action is made possible due to the fact that corresponding parts of the fixed part and the sliding part are linked by the linking part.

In this case, the tip end of the endoscope and the sheath can be oriented in any direction by rotating the endoscope in the axial direction together with the sheath, and by adjusting the length of insertion of the endoscope and the sheath. Furthermore, the fixed part is attached to the outer periphery at the tip end of the sheath, and therefore it does not obstruct observation by the endoscope of the stomach wall etc. By means of this, it is possible to change the direction of observation of the endoscope using a simple operation, enabling more reliable checking of the state of the stomach's inner walls, and more reliable confirmation of the indwelling position of the gastrostomy catheter. In this case it is also possible to use the endoscope to confirm the direction of the through-hole which opens at the intra-stomach fixed part. Furthermore, the endoscope is bent using the bending member, and therefore it is possible to adopt a simple structure in which the endoscope does not comprise a mechanism for bending itself. By means of this, it is possible to reduce the components of the endoscope which might fail.

Furthermore, the fixed part may be fixed to the sheath, or it may be detachable from the sheath. Once the inner walls of the stomach have been checked and the indwelling position of the gastrostomy catheter has been confirmed, the endoscope is pulled out from the gastrostomy catheter together with the sheath and the bending member, after which the endoscope can be removed from the patient's body without being soiled by gastric juices or the like, by pulling out the endoscope from the sheath. As a result, there is almost no need to sterilize or clean the endoscope, which makes sterilizing and cleaning costs almost unnecessary, and also the lifespan of the endoscope is extended.

Another structural feature of at least one embodiment of the bending instrument for an endoscope according to the present invention lies in the fact that the fixed part and the sliding part are annular. In this case, it is possible to make the fixed part and the sliding part into a cylinder shape or a ring shape, and this means that it is possible to obtain a bending member which has a simple structure and good operational performance. Furthermore, the fixed part, the sliding part and the linking part are preferably integrally moulded.

A further structural feature of an embodiment of the bending instrument for an endoscope according to the present invention lies in the fact that a protrusion is provided at a portion between the fixed part and the sliding part on the abovementioned sheath. In this case, when the fixed part is detachable from the sheath, the tip end of the sheath is formed tapering towards the end, and also the inner peripheral surface of the fixed part is formed as a curved surface which can engage with the tip end of the sheath; the protrusion which is formed on the sheath can act as a retaining protrusion for preventing the sliding part from being withdrawn from the tip end of the sheath.

Furthermore, when the fixed part is fixed to the sheath, the protrusion prevents the sliding part from moving towards the tip end of the sheath, and it is possible to contrive so that the sliding part is not prevented from being withdrawn when the bending instrument for an endoscope is withdrawn from the gastrostomy catheter. In addition, one protrusion or a plurality of protrusions may be provided. It is also possible to provide a plurality of protrusions in a continuous fashion in the axial direction of the sheath so as to form an accordion-like shape, and this allows the sheath to bend easily while preventing folding from occurring at the tip end side portion of the sheath.

A further structural feature of an embodiment of the bending instrument for an endoscope according to the present invention lies in the fact that the tip end portion of the sliding part is able to protrude outwards of the engagement part, and when the endoscope is pulled out from the gastrostomy catheter together with the sheath from a state in which the endoscope which is covered by the sheath passes inside the gastrostomy catheter and the tip end portion of the sliding part projects outwards of the engagement part, a resistance-imparting projection which temporarily engages with the engagement part so as to offer resistance when the tip end portion of the sliding part goes past the engagement part is provided at the tip end portion of the sliding part.

This simplifies the operation to remove the endoscope to which the bending instrument for an endoscope is fitted from the gastrostomy catheter. For example, when the endoscope which has bent a great deal together with the sheath and is projecting outwards of the tip end of the gastrostomy catheter is pulled out, if the whole of the sliding part retracts into the intra-stomach fixed-part, the tip end of the endoscope is pulled towards the engagement part via the fixed part, by means of the linking part, and the portion of the endoscope more towards the base end than the tip end takes on a circular shape, and a state is maintained in which it remains projecting outwards from the tip end of the gastrostomy catheter.

Consequently, by providing the resistance-imparting projection at the tip end portion of the sliding part, it makes it difficult for the sliding part to retract inside the intra-stomach fixed part, and in this state the endoscope and the sheath are pulled to retract them, whereby the bent state of the endoscope and the sheath can be lessened. Then, when the bent state of the endoscope and the sheath has been lessened, the endoscope and the sheath are pulled more, whereby the engagement of the resistance-imparting projection with the engagement part is released, and the endoscope can be withdrawn from the gastrostomy catheter together with the bending instrument for an endoscope.

The structural feature of at least one embodiment of the endoscope set according to the present invention lies in the fact that it is provided with the abovementioned bending instrument for an endoscope, the abovementioned gastrostomy catheter and the abovementioned endoscope. By means of this, an endoscope set can be produced with which it is possible to more reliably check the inner walls of the stomach and confirm the indwelling position of the gastrostomy catheter, and also with which there is no soiling of the endoscope by gastric juices etc. after use.

What is claimed:

1. Bending instrument for an endoscope comprising a tubular part having an internal through-hole extending to a tip end, and an intra-stomach fixed part joined to the tip end of the tubular part in a state in which the tip end of the through-hole of the tubular part is open and which is provided with an engagement part in the vicinity of the tip end of the through-hole; said instrument is used when an endoscope is inserted into a gastrostomy catheter which is indwelling in a gastrostomy hole in a state in which the tubular part is positioned in the gastrostomy hole formed between the surface of a patient's skin and the inner surface of the stomach wall and also in which the intra-stomach fixed part is positioned inside the stomach; said bending instrument for an endoscope being characterized in that it comprises: a sheath which can pass inside the gastrostomy catheter together with the endoscope in a state in which it covers the endoscope, and which has a light-transmissive window part formed at its tip end; and a bending member including a fixed part which is attached to the tip end outer periphery of the sheath in a state in which it cannot move to the base end side of the sheath and which can pass inside the gastrostomy catheter together with the sheath; a sliding part which is slidably attached further to the base end side of the sheath than the portion where the fixed part is attached, and which can pass through the through-hole of the gastrostomy catheter, and is configured to engage the engagement part of the intra-stomach fixed part so as not to be able to go past the intra-stomach fixed part; and a linking part which links the fixed part and the sliding part, controlling the gap between the fixed part and the sliding part so that it does not exceed a specified length; wherein the tip end portion of the sliding part is able to protrude outward beyond the engagement part, and when the endoscope is pulled out from the gastrostomy catheter together with the sheath from a state in which the endoscope covered by the sheath passes inside the gastrostomy catheter and the tip end portion of the sliding part projects outward from the engagement part, a resistance-imparting projection which temporarily engages with the engagement part so as to offer resistance when the tip end portion of the sliding part goes past the engagement part.

2. Bending instrument for an endoscope according to claim 1, wherein the fixed part and the sliding part are annular.

3. Bending instrument for an endoscope according to claim 1, in which a protrusion is provided at a portion between the fixed part and the sliding part on the sheath.

4. Bending instrument for an endoscope according to claim 1, in combination with the gastrostomy catheter and the endoscope.

* * * * *